US010450547B1

(12) United States Patent
Sun et al.

(10) Patent No.: US 10,450,547 B1
(45) Date of Patent: Oct. 22, 2019

(54) MEDIUM SYSTEM AND METHOD FOR EX VIVO EXPANSION OF NK CELLS

(71) Applicant: Purecell Biomedical Technology Company Limited, Hong Kong (CN)

(72) Inventors: Zhenhua Sun, Suzhou (CN); Hui Cao, Suzhou (CN)

(73) Assignee: PURECELL BIOMEDICAL TECHNOLOGY COMPANY LIMITED, Hong Kong (CN)

( * ) Notice: Subject to any disclaimer, the term of this patent is extended or adjusted under 35 U.S.C. 154(b) by 0 days.

(21) Appl. No.: 16/293,710

(22) Filed: Mar. 6, 2019

(30) Foreign Application Priority Data

Oct. 25, 2018 (CN) .......................... 2018 1 1250648

(51) Int. Cl.
*C12N 5/0783* (2010.01)
*C12N 5/00* (2006.01)
*C12N 5/0784* (2010.01)

(52) U.S. Cl.
CPC ......... *C12N 5/0646* (2013.01); *C12N 5/0018* (2013.01); *C12N 5/0639* (2013.01); *C12N 2501/22* (2013.01); *C12N 2501/2302* (2013.01); *C12N 2501/2304* (2013.01); *C12N 2501/2315* (2013.01); *C12N 2501/2321* (2013.01)

(58) Field of Classification Search
CPC .... A61K 45/06; A61K 38/20; A61K 38/1709; A61K 38/17; A61K 38/193; A61K 38/2026; C12N 2510/00; C12N 5/0646; C12N 2501/2302; C12N 2501/2321; C12N 15/85; C12N 2501/2315; C12N 5/0639; C12N 2501/2304; C12N 5/16; C12N 15/907; C12N 2500/84; C12N 2502/1164; C12N 2510/02; C12N 2513/00; C07K 14/54; C07K 14/5443; C07K 14/55; C07K 14/47; C07K 14/7155; C07K 16/244; C07K 16/3061; C07K 14/435; C07K 14/5406; G01N 2333/5443; G01N 33/6869
See application file for complete search history.

(56) References Cited

U.S. PATENT DOCUMENTS

| | | | |
|---|---|---|---|
| 10,113,148 B2 | 10/2018 | Abe et al. | |
| 2012/0148553 A1 | 6/2012 | Hariri et al. | |
| 2012/0171173 A1 | 7/2012 | Ideno et al. | |
| 2017/0333479 A1 | 11/2017 | Copik et al. | |
| 2018/0355317 A1 | 12/2018 | Shin | |

FOREIGN PATENT DOCUMENTS

| | | | |
|---|---|---|---|
| CN | 103756964 A | 4/2014 | |
| CN | 103923879 A | 7/2014 | |
| CN | 104593324 A | 5/2015 | |
| CN | 104789527 A | 7/2015 | |
| CN | 105296426 A | 2/2016 | |
| CN | 105462924 A | 4/2016 | |
| CN | 105754942 A | 7/2016 | |
| CN | 105925527 A | 9/2016 | |
| CN | 106011061 A | 10/2016 | |
| CN | 106085958 A | 11/2016 | |
| CN | 106148282 A | 11/2016 | |
| CN | 106434554 A | 2/2017 | |
| CN | 107022524 A | 8/2017 | |
| CN | 107083362 A | 8/2017 | |
| CN | 107099503 A | 8/2017 | |
| CN | 107326008 A | 11/2017 | |
| CN | 107460167 A | 12/2017 | |
| CN | 107779433 A | 3/2018 | |
| CN | 108004211 A | 5/2018 | |
| CN | 108624559 A | 10/2018 | |
| CN | 108642012 A | 10/2018 | |
| CN | 108676775 A | 10/2018 | |
| JP | 2013071915 A | 4/2013 | |
| WO | 2012009422 A1 | 1/2012 | |

OTHER PUBLICATIONS

Koepsell et al., 2012, "Natural killer cells: a review of manufacturing and clinical utility", Transfusion, 1-12.
Lim et al., 2013, "GMP-Compliant, Large-Scale Expanded Allogeneic Natural Killer Cells Have Potent Cytolytic Activity against Cancer Cells In Vitro and In Vivo", PLOS One, 8(1):e53611.
Masuyama et al., 2016, "Ex vivo expansion of natural killer cells from human peripheral blood mononuclear cells co-stimulated with anti-CD3 and anti-CD52 monoclonal antibodies", Cytotherapy, 918(1):80-90.
Torelli et al., 2015, "A good manufacturing practice method to exvivo expand natural killer cells for clinical use", Blood Transfus, vol. 13:464-71.
Bonanno et al., 2010, "Thymoglobulin, interferon-Y and interleukin-2 efficiently expand cytokine-induced killer (CIK) cells in clinical-grade cultures", Journal of Translational Medicine, 8:129.
Cho, Duck and Campana, Dario. 2009, "Expansion and Activation of Natural Killer Cells for Cancer Immunotherapy", Korean J Lab Med, 29: 89-96.

(Continued)

*Primary Examiner* — Lynn Y Fan
(74) *Attorney, Agent, or Firm* — Law Offices of Albert Wai-Kit Chan, PLLC

(57) ABSTRACT

This invention relates to a medium system and a method for ex vivo expansion of natural killer (NK) cells. This invention directly cultures Ficoll-separated PBMC by using immobilized anti-CD137 and RetroNectin, and uses OK-432 as a biological effector under the co-existence of GM-CSF, IL-4, IL-2, IL-15, and IL-21 for ex vivo activation and proliferation of NK cells, creating an efficient method for ex vivo expansion of NK cells. The expression rate of NK cells CD3-CD16+/CD56+ prepared by the method is as high as 92.5% or more. After 14 days of culture, NK cells can be expanded 1000 to 2000 times and have strong in vitro cytotoxic activity.

15 Claims, 4 Drawing Sheets

(56) References Cited

OTHER PUBLICATIONS

Garg et al., 2012, "Highly activated and expanded natural killer cells for multiple myeloma immunotherapy", Haematologica, 97(9): 1348-1356.

Ideno et al., 2011, "Novel neutral killer (NK)—cell expansion system for producing large amount (>109 cells) and high purity (>90%) of CD3+ CD56+ cells", Journal of Stem Cells & Regenerative Medicine, vol. 17, No. 3:135.

Lapteva et al., 2012, "Large-scale ex vivo expansion and characterization of natural killer cells for clinical applications", Cytotherapy, 14(9): 1131-1143.

Li et al., 2010, "Optimized Protocols for Generation of Cord Blood-derived Cytokine-induced Killer/Natural Killer Cells", Anticancer Research, 30: 3493-3500.

Liu et al., 2008, "Glucocorticoid-induced Tumor Necrosis Factor Receptor Negatively Regulates Activation of Human Primary Natural Killer (NK) Cells by Blocking Proliferative Signals and Increasing NK Cell Apoptosis", The Journal of Biological Chemistry, vol. 283, No. 13: 8202-8210.

Sun et al., 2011, "Homeostatic proliferation generates long-lived natural killer cells that respond against viral infection", The Journal of Experimental Medicine, vol. 208, No. 2: 357-368.

Itoh et al., 2003, "Streptococcal preparation OK432 promotes functional maturation of human monocyte-derived dendritic cells", Cancer Immunol Immunother, 52: 207-214.

Wu et al., 2018, "Induction of IL-2 in combination with IL-21 on human peripheral blood NK cells", Guangdong Medical Journal, vol. 39, No. 2: 192-198.

Ye Feng, 2017, "Study on killing effect of NK/iNKT cells and gamma-delta-T cells cultured in vitro to Jurkat, A549, K562 and HepG2 cell lines", China Master's Theses Full-text Database, Medical and Health Technology, Issue 9.

Yu Limei, Apr. 26, 2013, "The effects of OK-432 stimulated dendritic cells on expansion and function of natural killer cells", Wanfang Dissertation Public Database, China.

CNIPA Search Report, dated Jun. 12, 2019, for Purecell Biomedical Technology Company Limited, HK application No. 19123034.1, Filed Mar. 19, 2019.

CNIPA Search Report, dated Jun. 28, 2019, for Purecell Biomedical Technology Company Limited, HK application No. 19123033.3 Filed Apr. 26, 2019.

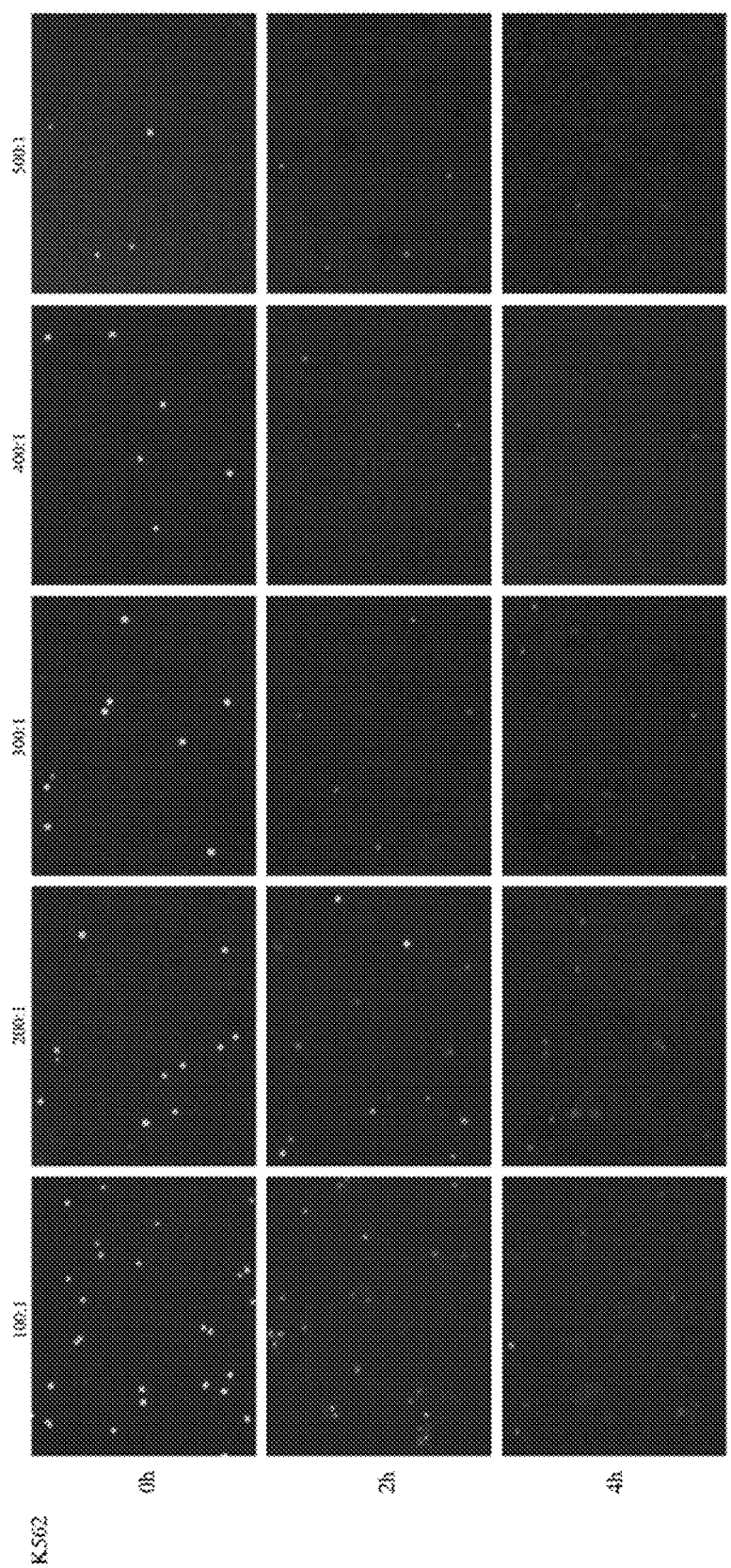

MEDIUM SYSTEM AND METHOD FOR EX VIVO EXPANSION OF NK CELLS

FIELD OF THE INVENTION

The present invention relates to the field of immunology, in particular to a medium system and a method for ex vivo expansion of natural killer cells.

BACKGROUND OF THE INVENTION

For a long time, surgery, radiotherapy and chemotherapy have been used as traditional methods to treat malignant tumors. However, these treatments are not effective for all tumors, and some are accompanied by obvious side effects. Therefore, finding a treatment method with small damage and effective control of tumor growth and metastasis has become an urgent need for clinical tumor treatment. With the rapid development and cross-infiltration of related disciplines such as oncology, immunology and molecular biology, research on tumor immunotherapy has advanced by leaps and bounds, and on the basis of immunological principles, cancer cell immunotherapy has been established based on cell biology techniques. It has evolved from laboratory research to effective and safe clinical applications.

SUMMARY OF THE INVENTION

Natural killer (NK) cells are a third type of lymphocytes other than T and B cells, and have unique cell subsets. NK cells are important immunologic effector cells and play an important role in fighting tumors and viral infections. In recent years, research on NK cells and their anti-tumor functions has become one of the highlights in immunology and oncology research. Anti-tumor function of NK cell has been extensively tested in countries such as the United States and Japan, showing good application prospects. The types of tumors that NK cells can treat clinically include, but are not limited to, adrenocortical carcinoma, AIDS-related cancer, melanoma, bladder cancer, brain tumor, central nervous system tumor, cervical cancer, chronic lymphocytic leukemia, colon cancer, colorectal cancer, breast cancer, endometrial cancer, esophageal cancer, oral cancer, pituitary tumor, T-cell lymphoma, nephroblastoma, thyroid cancer, etc.

The NK cell content in peripheral blood lymphocytes is only about 10%. The conventional method of ex vivo expansion uses high-dose IL-2 to expand NK cells, which can only be expanded by dozens of times, and requires a large amount of peripheral blood (more than 500 ml) from patient to achieve the number of cells needed for treatment. Therefore, the main obstacle to the clinical application of NK cells is how to obtain a sufficient number of NK cells to achieve high ex vivo expansion efficiency. Scientists all over the world have conducted fruitful research and have achieved certain results. According to reports, researchers used retrovirus to transfect CD137L and IL-15 into K562 cells, and obtained CD137L and IL-15 molecules with membrane expression. The cells were co-cultured with human peripheral blood mononuclear cells, and a large number of NK cells were obtained. However, the method is deficient in that the method of retroviral transfection is cumbersome to operate, which is not easy to generalize, and requires gamma rays to inactivate cells transfected with adenovirus, once the inactivation is insufficient, K652 cells which are cancer cells themselves will expand in the body, equivalent to artificially introducing cancer cells. Besides, there is a certain risk in using retroviruses, and the transgenic cells introduced in the culture system will eventually be mixed into the NK cell preparation.

BRIEF DESCRIPTION OF THE FIGURES

FIG. 4 shows the cytotoxic activity of the NK cells cultured in Example 1 against K562 by Calcein-AM assay;

DETAILED DESCRIPTION OF THE INVENTION

Figure 1:
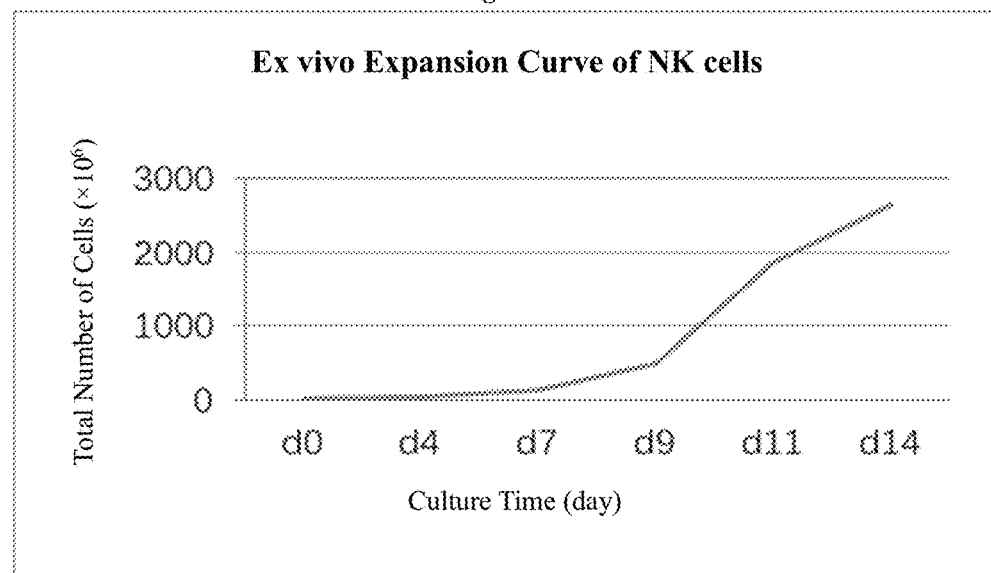
FIG. 1 shows an ex vivo expansion curve of NK cells cultured in Example 1.

The purpose of the present invention is to overcome the cumbersome and risky transgenic method, use cytokine alone to activate and expand NK cells, thereby creating an NK cell culture system with simple operation, low cost and high expansion efficiency, providing strong support for the clinical application of NK cells.

In one embodiment, the present invention employs the following technical scheme to achieve above-mentioned purpose:

Firstly, the present invention provides a medium system for ex vivo expansion of NK cells, comprising an induction medium and a proliferation medium, wherein the induction medium comprises a basic medium and a group of induction factors;

the group of induction factors comprises Ok-432, IL-2, IL-15, and IL-21;

the proliferation medium comprises a basic medium and a group of proliferation factors; and the group of proliferation factors comprises rhGM-CSF and rhIL-4.

In one embodiment, wherein said OK-432 can enhance the cytotoxicity of cells such as NK cells and lymphocytes, and promote the secretion of IFN-r, IL-2, TNF-α, etc., and regulate the anti-tumor immune response of the body. In one embodiment, wherein OK-432 is added as a biological effector to the culture medium at the initial stage of cell culture to activate NK cells; in addition, IL-2, IL-15 and IL-21 can maintain NK cell proliferation and survival. In one embodiment, OK-432 and IL-2, IL-15 and IL-21 are co-existent in the culture medium for initial stage of cell culture, which can effectively increase the expression rate of NK cells, making it up to 92.5%, and greatly improving the expansion fold of NK cells, enhancing the in vitro tumor-cytotoxic activity.

In one embodiment, wherein the GM-CSF and IL-4 can maintain the survival of DC cells, and further promote the ex vivo expansion of NK cells.

In one embodiment, wherein the group of induction factors comprises OK-432 at a concentration of 1~1.5 µg/ml. In various embodiments, the OK-432 is selected from OK-432 at a concentration of 1 µg/ml, 1.05 µg/ml, 1.1 µg/ml, 1.2 µg/ml, 1.25 µg/ml, 1.3 µg/ml, 1.35 µg/ml, 1.4 µg/ml, 1.45 µg/ml, or 1.5 µg/ml. In one embodiment, the concentration of OK-432 is 1 µg/ml.

In one embodiment, wherein the group of induction factors comprises IL-2 at a concentration of 500~750 IU/ml. In various embodiments, the IL-2 is selected from IL-2 at a concentration of 500 IU/ml, 520 IU/ml, 550 IU/ml, 580

IU/ml, 600 IU/ml, 620 IU/ml, 650 IU/ml, 680 IU/ml, 700 IU/ml, 720 IU/ml, or 750 IU/ml. In one embodiment, the concentration of IL-2 is 500 IU/ml.

In one embodiment, wherein the group of induction factors comprises IL-15 at a concentration of 15~30 ng/ml. In various embodiments, the IL-15 is selected from IL-15 at a concentration of 15 ng/ml, 16 ng/ml, 18 ng/ml, 20 ng/ml, 22 ng/ml, 25 ng/ml, 28 ng/ml, or 30 ng/ml. In one embodiment, the concentration of IL-15 is 20 ng/ml.

In one embodiment, wherein the group of induction factors comprises IL-21 at a concentration of 45~60 ng/ml. In various embodiments, the IL-21 is selected from IL-21 at a concentration of 45 ng/ml, 48 ng/ml, 50 ng/ml, 52 ng/ml, 54 ng/ml, 56 ng/ml, 58 ng/ml, or 60 ng/ml. In one embodiment, the concentration of IL-21 is 50 ng/ml.

In one embodiment, wherein the group of proliferation factors comprises rhGM-CSF at a concentration of 900~1200 U/ml. In various embodiments, the rhGM-CSF is selected from rhGM-CSF at a concentration of 900 U/ml, 920 U/ml, 950 U/ml, 1000 U/ml, 1050 U/ml, 1080 U/ml, 1100 U/ml, 1120 U/ml, 1150 U/ml, 1180 U/ml, or 1200 U/ml. In one embodiment, the concentration of rhGM-CSF is 1000 U/ml.

In one embodiment, wherein the group of proliferation factors comprises rhIL-4 at a concentration of 400~500 U/ml. In various embodiments, the rhIL-4 is selected from rhIL-4 at a concentration of 400 U/ml, 420 U/ml, 440 U/ml, 450 U/ml, 480 U/ml, 490 U/ml, or 500 U/ml. In one embodiment, the concentration of rhIL-4 is 500 U/ml.

In one embodiment, the medium system further comprises 5% autologous serum, 1% glutamine and 1% non-essential amino acids.

In various embodiments, the induction medium comprises: a basic medium, 5% autologous serum, 1% glutamine, 1% non-essential amino acids, OK-432 at a concentration of 1~1.5 µg/ml, IL-2 at a concentration of 500~750 IU/ml, IL-15 at a concentration of 15~30 ng/ml, and IL-21 at a concentration of 45~60 ng/ml.

In one embodiment, the induction medium comprises: a basic medium, 5% autologous serum, 1% glutamine, 1% non-essential amino acids, OK-432 at a concentration of 1 µg/ml, IL-2 at a concentration of 500 IU/ml, IL-15 at a concentration of 20 ng/ml, and IL-21 at a concentration of 50 ng/ml.

In various embodiments, the proliferation medium comprises: a basic medium, 5% autologous serum, 1% glutamine, 1% non-essential amino acids, rhGM-CSF at a concentration of 900~1200 U/ml, and rhIL-4 at a concentration of 400~500 U/ml.

In one embodiment, the proliferation medium comprises: a basic medium, 5% autologous serum, 1% glutamine, 1% non-essential amino acids, rhGM-CSF at a concentration of 1000 U/ml, and rhIL-4 at a concentration of 500 U/ml.

In one embodiment, the basic medium may be a basic medium well known in the art, such as RPMI-1640 medium, etc., and is not particularly limited.

Herein, the terms "autologous serum", "glutamine", "non-essential amino acids", OK-432, IL-2, IL-15, IL-21, rhGM-CSF and rhIL-4 have the meaning known in the art. Those skilled in the art can use any commercially available products according to their actual needs, and the source thereof is not particularly limited.

In one embodiment, the present invention can effectively increase the expression rate of NK cells by adding a combination factor in the induction medium and the proliferation medium, so as to increase the expression rate of NK cells by more than 92.5%, and greatly increase the expansion fold of NK cells, which is 1000 to 2000 times, and enhance the in vitro tumor-cytotoxic activity.

Secondly, the present invention provides a method for ex vivo expansion of NK cells, comprising stage-by-stage and successive uses of the above-mentioned induction medium and proliferation medium.

In one embodiment, the method for ex vivo expansion of NK cells comprises culturing Ficoll-separated PBMC by using immobilized anti-CD137 and RetroNectin.

In one embodiment, the present invention adopts the immobilized CD137 monoclonal antibody to bind with the CD137 molecule of NK cells, activates the CD137 costimulatory signal pathway, promoting the activation and proliferation of NK cells. RetroNectin can strongly promote the ex vivo expansion of immune cells, and its mechanism is: promoting adhesion between cells, enhancing signal transduction; inducing cell activation and expansion; resisting apoptosis of activated cell; and promoting cells move from G1 phase into S phase. The present invention uses the immobilized RetroNectin to culture NK cells, promoting NK cell proliferation while avoiding apoptosis caused by cell expansion. In summary, the present invention utilizes immobilized anti-CD137 and RetroNectin for pre-coating cell culture flasks and directly culturing Ficoll-separated PBMC. The combination of anti-CD137 and RetroNectin has synergistic efficacy. It not only promotes the activation and proliferation of NK cells, but also effectively avoids apoptosis caused by cell expansion.

Herein, the terms "anti-CD137", "RetroNectin" have the meaning known in the art. Those skilled in the art can use any commercially available products according to their actual needs, and the source thereof is not particularly limited.

In one embodiment, the process of culturing Ficoll-separated PBMC by using immobilized anti-CD137 and RetroNectin comprises following steps:

Adding 5 ml DPBS to each of the two cell culture flasks; adding anti-CD137 at a concentration of 5 µg/ml to cell culture flask 1; adding RetroNectin at a concentration of 5 µg/ml to cell culture flask 2; storing overnight at 4° C.; discarding the DPBS, and washing three times with additional DPBS;

Re-suspending the isolated PBMC in the induction medium at a concentration of $5 \times 10^5$/ml, inoculating said cells in said flask 1 for 2 hours; transferring the suspended cells from flask 1 into cell culture flask 2; and culturing the adherent DC cells in flask 1 with the proliferation medium for 24 hours.

In one embodiment, the method of ex vivo expansion of NK cells comprises following steps:
 (1) Pre-coating cell culture flasks 1 and 2 with anti-CD137 and RetroNectin, respectively;
 (2) Isolating peripheral blood mononuclear cells (PBMC);
 (3) Re-suspending the isolated PBMC in the induction medium, inoculating said cells in said flask 1; transferring the suspended cells in cell culture flask 1 into cell culture flask 2 and culturing the adherent DC cells in said flask 1 with the proliferation medium;
 (4) Re-suspending the adherent DC cells in said flask 1 when they mature, and adding the cells into flask 2, supplemented with rhGM-CSF and rhIL-4;
 (5) Continuing to culture until day 4, when IL-2, IL-15, and IL-21 are added; and
 (6) Culturing until harvest.

In one embodiment, the pre-coating process in step (1) comprises: adding 5 ml DPBS to each of the two cell culture flasks; adding anti-CD137 at a concentration of 5 µg/ml and RetroNectin at a concentration of 5 µg/ml to said flask 1 and said flask 2, respectively; storing overnight at 4° C.; discarding the DPBS; and washing three times with additional DPBS.

In one embodiment, the method of ex vivo expansion of NK cells comprises following steps:
(1) Adding 5 ml DPBS to each of the two cell culture flasks; adding anti-CD137 at a concentration of 5 µg/ml to cell culture flask 1; adding RetroNectin at a concentration of 5 µg/ml to cell culture flask 2; storing overnight at 4° C.; discarding the DPBS; and washing three times with additional DPBS.
(2) Diluting 50 ml of aseptic peripheral blood with DPBS at a ratio of 1:2 to obtain 150 ml of diluted blood; adding 15 ml of Ficoll separation solution at a density of 1.077 to each of five 50 ml centrifuge tubes; adding 30 ml of the diluted blood to each tube; centrifuging at 800 g for 30 minutes; and obtaining PBMC after washing;
(3) Re-suspending the obtained PBMC in the induction medium at a concentration of $5 \times 10^5$/ml; inoculating in said flask 1 for 2 hours; transferring the suspended cells from flask 1 into flask 2; and culturing the adherent DC cells in flask 1 with the proliferation medium for 24 hours;
wherein the induction medium comprises basic medium, 5% autologous serum, 1% glutamine and 1% non-essential amino acids, 1 µg/ml OK-432, 500 IU/ml IL-2, 20 ng/ml IL-15, and 50 ng/ml IL-2;
wherein the proliferation medium comprises basic medium, 5% autologous serum, 1% glutamine and 1% non-essential amino acids, 1000 U/ml rhGM-CSF, and 500 U/ml rhIL-4;
(4) Suspending the adherent DC cells in flask 1 when they mature after culturing for 24 hours; transferring the DC cells in flask 1 to a 50 ml centrifuge tube; centrifuging at 1000 rpm for 10 minutes; re-suspending and adding into flask 2 followed by adding 1000 U/ml rhGM-CSF and 500 U/ml rhIL-4;
(5) Continuing to culture until day 4 when 500 IU/ml IL-2, 20 ng/ml IL-15, and 50 ng/ml IL-21 are added; and
(6) Continuing to culture until day 7 when more cell culture flasks are used for culturing until day 14 when NK cells are harvested.

In one embodiment, the method for ex vivo expansion of the NK cells of the present invention is: directly culturing Ficoll-separated PBMC by using immobilized anti-CD137 and RetroNectin, and using OK-432 as a biological effector under the co-existence of GM-CSF, IL-4, IL-2, IL-15, and IL-21 for ex vivo activation and proliferation of natural killer (NK) cells. The expression rate of NK cells CD3-CD16+/CD56+ prepared by the method is as high as 92.5% or more. After 14 days of culture, NK cells can be expanded 1000 to 2000 times.

Compared with the prior art solutions, the present invention has at least the following beneficial effects:
(1) The present invention induces and promotes ex vivo expansion of NK cells using an immobilized anti-human CD137 monoclonal antibody, and OK-432 provides an initial activation environment for NK cells as a biological effector, and RetroNectin enhances NK cell expansion efficiency and avoids apoptosis caused by cell proliferation;
(2) The present invention creates a highly efficient method for ex vivo expansion of NK cells. The expression rate of NK cells CD3-CD16+/CD56+ prepared by the method is as high as 92.5% or more. After 14 days of culture, NK cells can be expanded 1000 to 2000 times.

The invention will be better understood by reference to the Experimental Details which follow, but those skilled in the art will readily appreciate that the specific experiments described are only for illustrative purpose and are not meant to limit the invention as described herein, which is defined by the claims that follow thereafter.

Throughout this application, various references or publications are cited. Disclosures of these references or publications in their entireties are hereby incorporated by reference into this application in order to more fully describe the state of the art to which this invention pertains. It is to be noted that the transitional term "comprising", which is synonymous with "including", "containing" or "characterized by", is inclusive or open-ended and does not exclude additional, un-recited elements or method steps.

Example 1

(1) Pre-coating cell culture flasks:
Adding 5 ml DPBS to each of the two T75 cell culture flasks; adding anti-CD137 at a concentration of 5 µg/ml to cell culture flask 1; adding RetroNectin at a concentration of 5 µg/ml to cell culture flask 2; storing overnight at 4° C.; flask 1 is used to promote maturation of DC cell, and flask 2 is used for activation and proliferation of NK cell.

(2) Preparation of induction medium and proliferation medium:
The induction medium comprises: a basic medium, 5% autologous serum, 1% glutamine, 1% non-essential amino acids, 1 µg/ml OK-432, 500 IU/ml IL-2, 20 ng/ml IL-15, and 50 ng/ml IL-21;
The proliferation medium comprises: a basic medium, 5% autologous serum, 1% glutamine, 1% non-essential amino acids, 1000 U/ml rhGM-CSF, and 500 U/ml rhIL-4.

(3) Pretreatment of Ficoll separation solution
Adding 1 ml of DPBS to 250 ml of Ficoll separation solution with a density of 1.077, shaken up for use.

(4) Diluting 50 ml of aseptic peripheral blood with DPBS at a ratio of 1:2 to obtain 150 ml of diluted blood; adding 15 ml of Ficoll separation solution with a density of 1.077 to each of five 50 ml centrifuge tubes; adding 30 ml of the diluted blood to each tube; centrifuging at 800 g for 30 minutes; and obtaining PBMC after washing;

(5) Re-suspending the obtained PBMC in the induction medium at a concentration of $5 \times 10^5$/ml; inoculating in said flask 1 for 2 hours; transferring the suspended cells from flask 1 into flask 2; and culturing the adherent DC cells in flask 1 with the proliferation medium for 24 hours;
Suspending the adherent DC cells in flask 1 when they mature after culturing for 24 hours; transferring the DC cells in flask 1 to a 50 ml centrifuge tube; centrifuging at 1000 rpm for 10 minutes; re-suspending and adding into flask 2 followed by adding 1000 U/ml rhGM-CSF and 500 U/ml rhIL-4;

(6) Continuing to culture until day 4 when 500 IU/ml IL-2, 20 ng/ml IL-15, and 50 ng/ml IL-21 are added; and (7) Continuing to culture until day 7 when more cell culture flasks are used for culturing until day 14 when NK cells are harvested.

Example 2

In addition to Example 1, the culture medium in step (2) is prepared as below:

The induction medium comprises: Cellgro basic medium, 5% autologous serum, 1% glutamine, 1% non-essential amino acids, 1.5 μg/ml OK-432, 750 IU/ml IL-2, 30 ng/ml IL-15, and 60 ng/ml IL-21;

The proliferation medium comprises: Cellgro basic medium, 5% autologous serum, 1% glutamine, 1% non-essential amino acids, 1200 U/ml rhGM-CSF, and 500 U/ml rhIL-4.

Other steps and conditions are the same as in the Example 1.

Example 3

In addition to Example 1, the culture medium in step (2) is prepared as below:

The induction medium comprises: Cellgro basic medium, 5% autologous serum, 1% glutamine, 1% non-essential amino acids, 1 μg/ml OK-432, 500 IU/ml IL-2, 15 ng/ml IL-15, and 45 ng/ml IL-21;

The proliferation medium comprises: Cellgro basic medium, 5% autologous serum, 1% glutamine, 1% non-essential amino acids, 900 U/ml rhGM-CSF, and 400 U/ml rhIL-4.

Other steps and conditions are the same as in the Example 1.

Example 4

Since the cases of the NK cells cultured in Example 2-3 are similar to that of Example 1, the cells cultured in Example 1 are subjected to the subsequent tests.

Prepare 0.4% trypan blue solution, adjust its pH value to 7.0-7.2. Take 50 μl of NK cell suspension cultured on the $0^{th}$ day, the $4^{th}$ day, the $7^{th}$ day, the $9^{th}$ day, the $11^{th}$ day, and the $14^{th}$ day of Example 1, respectively. Add 50 μl of trypan blue to each of the NK cell suspension, stain the cells for 4 min, and the total number of cells is counted by hematocytometer.

As shown in FIG. 1, the proliferation of NK cells begins to show logarithmic growth on the $9^{th}$ day of culture, and on the $14^{th}$ day, the number of cells reaches $2700 \times 10^6$.

Example 5 Surface Marker Expression of NK Cells (Flow Detection)

Take 0.2 ml of the NK cell suspension of Example 1 which cultured to the $14^{th}$ day, wash twice with DPBS. Add 20 μl of FITC-CD3 CD16/CD56-PE, and store at 4° C. for 30 min. The purity of NK is measured via a flow cytometer under direct immunofluorescence.

Figure 2A:
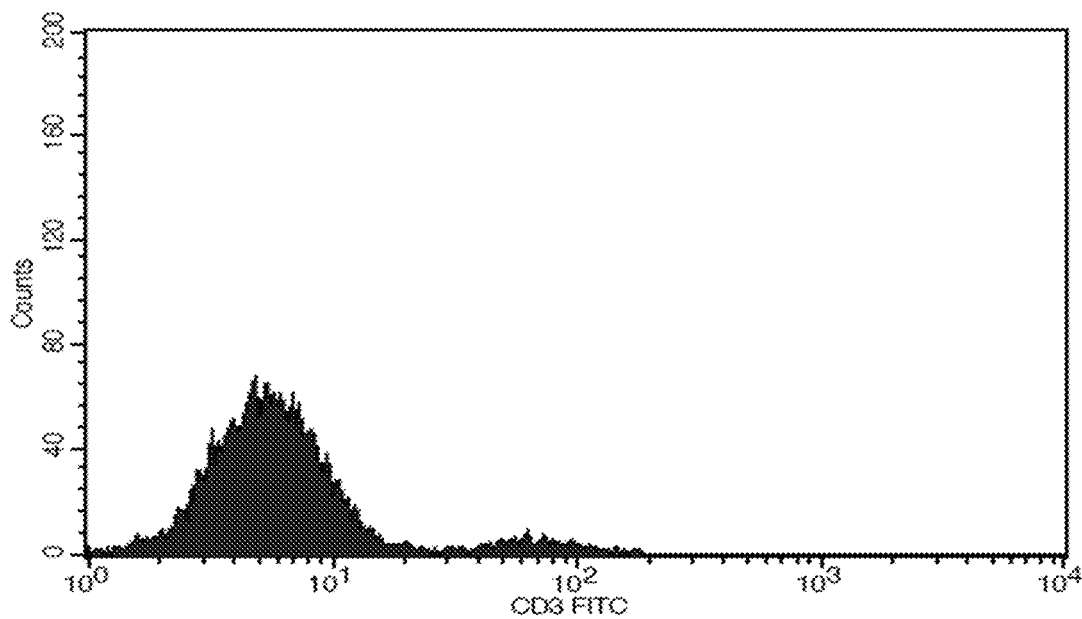
FIGS. 2A, 2B and 2C show the results of flow cytometry of NK cells cultured in Example 1.
Figure 2B:
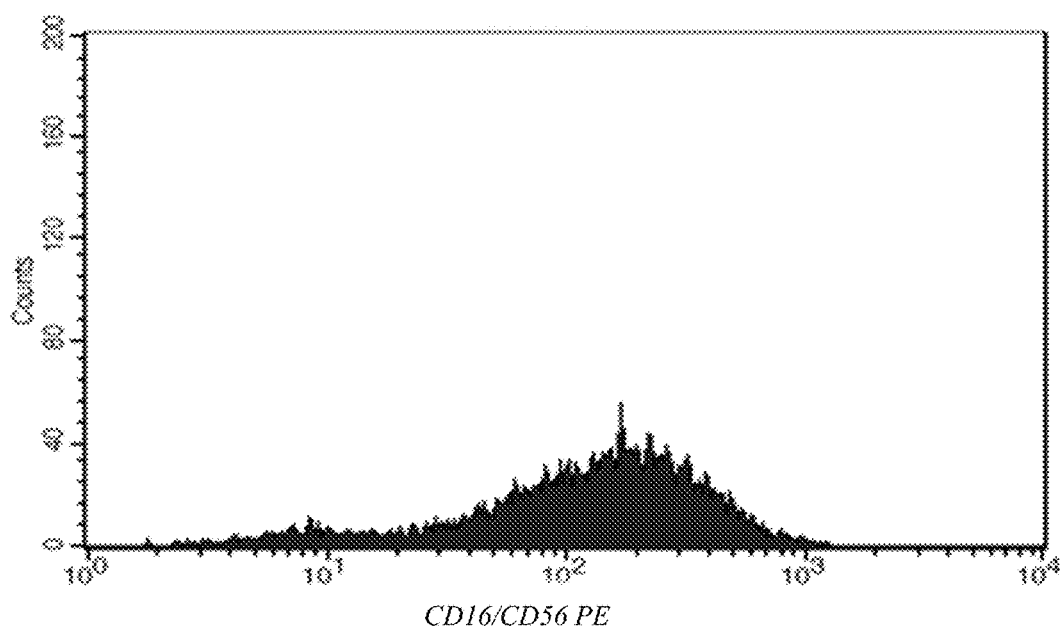
Figure 2C:
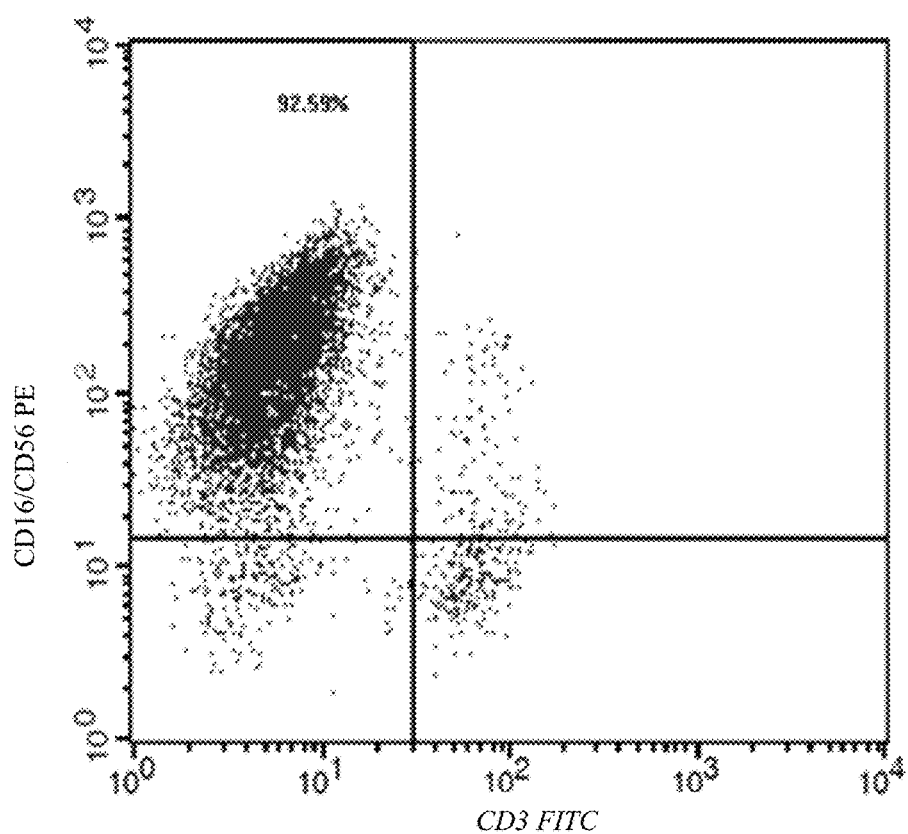

As shown in FIG. 2A, FIG. 2B, FIG. 2C, the content of NK cells is greatly increased after culturing to the $14^{th}$ day, and the expression rate, i.e. the purity of NK cells can reach 92.59%.

Example 6 In Vitro Cytotoxic Activity of NK Cells (MTT Assay)

Set three experimental groups, three pure effector cell groups, three pure target cell groups and control groups on the 96-well flat-bottomed plate. Add K562 to the experimental groups and pure target cell groups. Add NK cells cultured for 14 days in Example 1 to each of the experimental groups and the pure effector cell groups, and the effector-to-target ratios are set as 5:1, 10:1, 20:1, and 40:1, and culture for 24 hours. Add 20 μl of WST, continue to culture for 4 hours, and measure the Optical Density (OD) value by an enzyme-labeled instrument.

Cytotoxic activity (%)=[1−(OD value of experimental group−OD value of pure effector cell group)×OD value of pure target cell]×100%.

Figure 3:
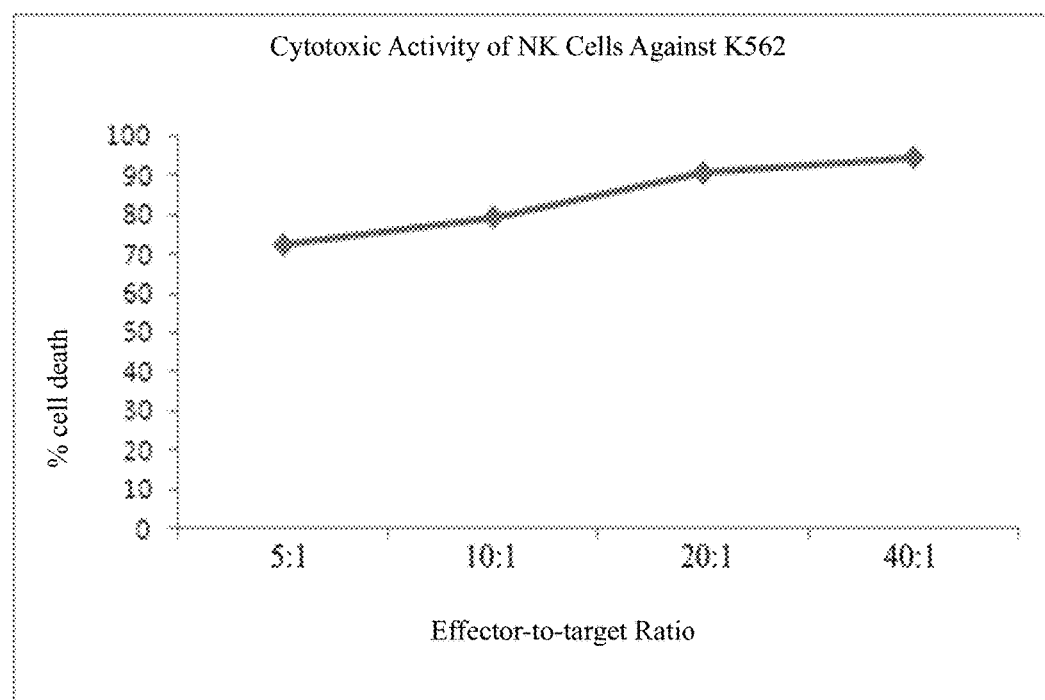
FIG. 3 shows the cytotoxic activity of the NK cells cultured in Example 1 against K562 by MTT assay.

As shown in FIG. 3, NK cells exert strong cytotoxic activity after co-culture with K562 cells and PC-3 cells for 24 hours, respectively, in the range of 5:1~40:1 effector-to-target ratio; and the higher the effector-to-target ratio is, the stronger the in vitro cytotoxic activity will be.

Example 7 In Vitro Cytotoxic Activity of NK Cells (Calcein-AM Assay)

Set three experimental groups, three pure effector cell groups, three pure target cell groups and control groups on the 96-well flat-bottomed plate. Add K562 labeled with Calcein-AM (green fluorescent labeled living cell) to the experimental groups and pure target cell groups. Add NK cells cultured for 21 days in Example 1 to each of the experimental groups and the pure effector cell groups, and the effector-to-target ratios are set as 500:1, 400:1, 300:1, 200:1, and 100:1. After 4 hours, observe results and photograph by fluorescence microscope.

As shown in FIG. 4, the cytotoxic activity of PBMC before culture is relatively low, and the cytotoxic activity gradually increase with the increase of culture time. With K562 as the target cell, NK cells exert their cytotoxic activity in a short time in the range of 100:1~500:1 effector-to-target ratio. After 2 hours, a large number of NK cells migrate to the target cells, surrounding the tumor cells, and start to kill the tumor cells by releasing cytotoxic factors or cytokines, or via ADCC. Some tumor cells have undergone apoptosis (fluorescence is weakened). After 4 hours, most tumor cells are in an apoptotic state (fluorescence is weakened or absent); and the higher the effector-to-target ratio is, the stronger the cytotoxic activity will be.

From the above results, it can be concluded that the present invention creates a highly efficient method for ex vivo expansion of NK cells. The expression rate of NK cells CD3-CD16+/CD56+ prepared by the method is as high as 92.5% or more. After 14 days of culture, NK cells can be expanded 1000 to 2000 times and have strong in vitro cytotoxic activity.

The applicant claims that the detailed structural features of the present invention are described by the above-described embodiments, but the present invention is not limited to the above detailed structural features, that is, the present invention is not achievable only via the above detailed structural features. It is to be understood by those skilled in the art that any modifications of the present invention, equivalent substitutions of the components selected for the present invention, and the addition of the components, the selection of the specific means, and the like, are all within the scope of the present invention.

The preferred embodiments of the present invention have been described in detail above, but the present invention is not limited to the specific details of the above embodiments, and various simple modifications can be made to the technical solutions of the present invention within the scope of the technical idea of the present invention. These simple variants all fall within the scope of protection of the present invention.

It should be further noted that the specific technical features described in the above specific embodiments may be combined in any suitable manner without contradiction. To avoid unnecessary repetition, the present invention does not describe the various possibilities of the combinations separately.

In addition, any combination of various embodiments of the invention may be made as long as it does not deviate from the idea of the invention, and it should be regarded as the disclosure of the invention.

What is claimed is:

1. A method for ex vivo expansion of natural killer (NK) cells, comprising:
   1) culturing a population of peripheral blood mononuclear cells (PBMC) in an induction medium comprising a basic culture medium and a group of induction factors comprising OK-432, IL-2, IL-15, and IL-21; and
   2) culturing the cells obtained from step (1) in a proliferation medium comprising a basic culture medium and a group of proliferation factors comprising rhGM-CSF and rhIL-4, wherein a population of NK cells is obtained.

2. A method for ex vivo expansion of natural killer (NK) cells, comprising the steps of:
   a) culturing peripheral blood mononuclear cells (PBMC) using an induction medium in a first cell culture flask pre-coated with anti-CD137, wherein said induction medium comprises a basic culture medium and a group of induction factors comprising OK-432, IL-2, IL-15, and IL-21;
   b) transferring suspension cells from the first cell culture flask to a second cell culture flask pre-coated with RetroNectin;
   c) culturing adherent dendritic cells in the first cell culture flask using a proliferation medium, wherein said proliferation medium comprises a basic culture medium and a group of proliferation factors comprising rhGM-CSF and rhIL-4; and
   d) collecting and transferring suspended non-adherent dendritic cells in the first cell culture flask to the second cell culture flask and culturing cells in said second culture flask using said proliferation medium for a period of time, thereby obtaining the population of NK cells.

3. A method for ex vivo expansion of natural killer (NK) cells, comprising the steps of:
   a) providing peripheral blood mononuclear cells (PBMC) to a first cell culture flask pre-coated with anti-CD137 and culturing said PBMC using an induction medium, wherein said induction medium comprises a basic culture medium and a group of induction factors comprising OK-432, IL-2, IL-15, and IL-21;
   b) transferring suspension cells from said first cell culture flask to a second cell culture flask pre-coated with RetroNectin;
   c) culturing adherent dendritic cells in said first cell culture flask using a proliferation medium, wherein said proliferation medium comprises a basic culture medium and a group of proliferation factors comprising rhGM-CSF and rhIL-4;
   d) collecting non-adherent dendritic cells from the first cell culture flask after step c) and transferring the collected non-adherent dendritic cells to the second cell culture flask;
   e) culturing cells in said second cell culture flask using the proliferation medium for a first period of time; and
   f) adding IL-2, IL-15 and IL-21 to said second cell culture flask and culturing the cells for a second period of time, thereby obtaining the population of NK cells.

4. The method of claim 3, wherein the first cell culture flask is pre-coated with anti-CD137 at a concentration of 5 µg/mL.

5. The method of claim 3, wherein the second cell culture flask is pre-coated with RetroNectin at a concentration of 5 µg/mL.

6. The method of claim 3, wherein the first period of time is four to six days.

7. The method of claim 3, wherein the second period of time is three days or more.

8. The method of claim 3, wherein the population of NK cells is obtained at least 14 days after the start of step e).

9. The method of claim 3, wherein the population of NK cells is obtained at least 21 days after the start of step e).

10. The method of claim 7, producing a population of NK cells wherein at least 90% of the NK cells are CD3-CD16+/CD56+.

11. The method of claim 3, wherein the induction medium contains OK-432 at a concentration of 1 µg/mL, IL-2 at a concentration of 500 IU/mL, IL-15 at a concentration of 20 ng/mL, and IL-21 at a concentration of 50 ng/mL.

12. The method of claim 3, wherein the proliferation medium contains rhGM-CSF at a concentration of 1000 U/mL and rhIL-4 at a concentration of 500 U/mL.

13. The method of claim 3, wherein the induction factors in step f) comprises IL-2 at a concentration of 500 IU/mL, IL-15 at a concentration of 20 ng/mL, and IL-21 at a concentration of 50 ng/mL in a basic culture medium.

14. The method of claim 13, wherein the number of NK cells in said population of NK cells is at least $2500 \times 10^6$.

15. The method of claim 8, wherein the number of NK cells in said population of NK cells is 1000 to 2000 times higher than the number of NK cells in the PBMC provided in step a).

* * * * *